United States Patent
Jacquot et al.

(10) Patent No.: US 6,541,674 B2
(45) Date of Patent: Apr. 1, 2003

(54) PROCESS FOR THE CONDENSATION OF A CARBONYL COMPOUND WITH AN AROMATIC DERIVATIVE IN A BASIC MEDIUM

(75) Inventors: Roland Jacquot, Francheville (FR); Michel Spagnol, Meyzieu (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/725,196

(22) Filed: Nov. 29, 2000

(65) Prior Publication Data

US 2001/0004670 A1 Jun. 21, 2001

Related U.S. Application Data

(63) Continuation-in-part of application No. PCT/FR99/01235, filed on May 26, 1999.

(51) Int. Cl.$^7$ .................. C07C 33/46; C07C 39/04; C07C 22/08
(52) U.S. Cl. .............. 568/812; 568/716; 568/780; 570/128
(58) Field of Search ............ 570/128; 568/716, 568/780, 812

(56) References Cited

U.S. PATENT DOCUMENTS 4,283,537 A * 8/1981 Cincotta et al. .............. 546/94

OTHER PUBLICATIONS

Caplus, english Abstrac AN#81:43572, Registry #75077–68–8p. Aug. 11, 1981 Cincotta et al.*

* cited by examiner

*Primary Examiner*—Alan L. Rotman
*Assistant Examiner*—Rita Desai
(74) *Attorney, Agent, or Firm*—Burns, Doane, Swecker & Mathis, L.L.P.

(57) ABSTRACT

A process for condensing at least one carbonyl compound carrying at least one electron-withdrawing group with an aromatic derivative carrying at least one hydroxyl functional group, wherein the electron-withdrawing group present on the carbonyl compound is selected from fluoroalkyl derivatives, esters, including orthoesters, and nitriles and said condensation is carried out in a basic medium.

51 Claims, No Drawings

PROCESS FOR THE CONDENSATION OF A CARBONYL COMPOUND WITH AN AROMATIC DERIVATIVE IN A BASIC MEDIUM

This application is a continuation-in-part of International Application No. PCT/FR99/01235 filed on May 26, 1999, which designates the United States of America and was published under PCT Article 21(2) in English on Dec. 9, 1999 and claims benefit of French Application 98 06848 filed on May 29, 1998. This application is incorporated by reference in its entirety.

The present invention relates to a process which makes it possible to condense, in a basic medium, one or more carbonyl compounds with aromatic derivatives.

A more specific object of the present invention is to provide a novel synthetic route for functionalizing aromatic derivatives with one or more carbonyl derivatives which advantageously does not require the formation of an intermediate.

The Applicant Company has unexpectedly demonstrated that it is possible to efficiently condense, in a single stage, at least one carbonyl derivative carrying at least one electron-withdrawing group, like, for example, fluoral, with an aromatic derivative.

This novel access route to functionalized aromatic derivatives is all the more advantageous industrially as these compounds are important synthetic intermediates in the preparation of compounds with pharmacological or plant-protection activity or of materials such as liquid crystals and/or pigments.

A subject-matter of the present invention is consequently a process for condensing at least one carbonyl compound carrying at least one electron-withdrawing group with an aromatic derivative carrying at least one hydroxyl functional group, wherein the electron-withdrawing group present on the carbonyl compound is selected from fluoroalkyl derivatives, esters, including orthoesters, and nitriles and said condensation is carried out in a basic medium.

A non-nitrogenous basic medium will be favored in the context of the present invention.

The claimed process is particularly advantageous since it allows to condense one or several molecules of a carbonyl compound with an aromatic derivative.

In fact, it is possible to control the condensation number per aromatic by various means like in particular the temperature of the reaction of condensation (the lower the temperature, the lower the number of condensation), the ratio between carbonyl compound and the aromatic, and/or the presence of some substituents on the aromatic cycle.

Thus, the condensation of carbonyl compound(s) with an aromatic derivative can be carried out in accordance with the present invention according to several alternative forms.

Generally, one of the best way to control the number of condensed carbonyl derivative per aromatic is to act on the molar ratio between carbonyl compound and the aromatic (carbonyl compound/aromatic). For a mono condensation, specially when said aromatic presents more than one position, the chose ratio is at most ½ and preferably of at most ¼ equivalents of aromatic value.

In other words, the latter value constitutes an excellent compromise for obtaining the condensation of a single carbonyl compound with the aromatic derivative. Thus, according to a specific form of the invention, the condensation is carried out in the presence of a stoechiometrical deficiency of carbonyl compound, in particular by using the carbonyl derivative in a ratio of 0.25 to 1 and preferably of 0.25 to 0.5 equivalents of aromatic derivative.

According to the second alternative form, when there is no risk of further condensation, this condensation is carried out in the presence of a stoechiometrical excess of carbonyl compound. To this end, it is preferably carried out using the carbonyl derivative in a ratio of at most 1 to 2 and preferably of at most 1 to 1.25 equivalents of aromatic derivative.

As regards more particularly the other parameters of the reaction, namely the time or the temperature, their adjustment is generally a function of the electron density of the aromatic derivative to be functionalized and of the $pK_a$ of the base used.

Generally, the condensation reaction is preferably carried out with heating. To this end, the reaction medium can be brought to a temperature of between approximately 40 and 100° C. and preferably of the order of 50° C. This heating is carried out in a way which is sufficiently prolonged over time to produce an optimum degree of conversion, DC, of the aromatic derivative.

For a temperature of greater than 50° C., it is possible to observe the condensation of several carbonyl compounds with the aromatic derivative.

However, it is clear that such a risk of polycondensation does not exist for some aromatics as they have for example substituents on some reactive positions. It is then possible to increase the reaction temperature above 50° C. for the sole purpose of reducing the time necessary for the condensation.

With regards to the substituents present on the aromatic cycle, the reactive positions of the aromatic cycle are the carbon atoms positioned in ortho and para to the hydroxyl functional group.

Accordingly, the presence of substituents in one or several of these three positions allows to direct the rate of condensation of the carbonyl compound at the aromatic ring.

As regards more particularly the carbonyl compound, the electron-withdrawing group is preferably positioned alpha to the carbonyl functional group.

The term "electron-withdrawing group" is understood to mean a group as defined by H. C. Brown in the work by Jerry March, "Advanced organic Chemistry", 3rd edition, chapter 9, pages 243 and 244.

This electron-withdrawing group is preferably characterized by a $\sigma_p$ at least equal to 0.30 and advantageously greater than or equal to 0.40 and less than 0.75 and preferably less than 0.65.

According to a preferred form of the invention, the electron-withdrawing group present on the carbonyl derivative is a fluoroalkyl derivative, advantageously a polyfluoroalkyl derivative.

As regards the corresponding alkyl group, it can be in particular a linear or branched $C_1$ to $C_{15}$, preferably $C_1$ to $C_{10}$, group. In addition to the required fluorine atom or atoms, this alkyl group can comprise other substituents, such as other halogen atoms, like chlorine, for example. Of course, these other substituents must remain inert during the condensation reaction.

The number of fluorine atoms present on this alkyl group can vary significantly insofar as these fluorine atoms confer, if appropriate in combination with the other substituents present on the alkyl group, a $\sigma_p$ in accordance with the present invention.

According to a preferred form of the invention, the electron-withdrawing group is a polyfluoroalkyl derivative corresponding to a radical of formula:

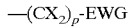
—(CX$_2$)$_p$-EWG in which
the X units, which are identical or different, are a hydrogen atom, a halogen atom, preferably fluorine, or a radical of formula $C_nX_{2n+1}$ with n being an integer at most equal to 5, preferably to 2;

p is an integer at most equal to 2;

the symbol EWG is an electron-withdrawing group, the possible functional groups of which are inert under the reaction conditions, advantageously a fluorine atom or a perfluorinated residue of formula $C_{n'}X_{2n'+1}$ with n' being an integer at most equal to 8, advantageously to 5, with the proviso that at least one of the X or EWG units present on the carbon α to the carbonyl functional group is a fluorine atom, and with the total number of carbon atoms of the polyfluoroalkyl derivative between 1 and 15, preferably between 1 and 10.

The polyfluorinated derivatives and in particular those defined by the preceding formula in which X is a fluorine atom or an EWG group with EWG being a fluorine atom or a perfluorinated residue of formula $C_{n'}X_{2n'+1}$ are very particularly suitable as polyfluorinated derivative.

In addition to the electron-withdrawing group as defined above, the carbonyl compound to be condensed can carry, at its carbonyl functional group, either a hydrogen atom or a group selected from $C_5$ to $C_{18}$ aryls, linear or branched $C_1$ to $C_{13}$ alkyls or linear or branched $C_2$ to $C_{14}$ alkenyls, if appropriate substituted. The substituents can in particular be a hydroxyl group, a halogen atom, a $C_1$–$C_{11}$ alkyl group and/or an amino group.

In addition, it is possible for the two substituents of the carbonyl functional group to be bonded to one another to form a $C_4$ to $C_8$ ring.

Mention may be in particular be made, as carbonyl derivatives very particularly suitable for the invention, of fluorinated aldehyde derivatives like perfluoroacetaldehyde, perfluoropropionaldehyde, perfluorobutyraldehyde, perfluorooctanal or perfluorobenzaldehyde type, any partially or completely fluorinated alkyl aldehyde derivative with a linear or branched chain having from 2 to 13 carbon atoms and any partially or completely fluorinated aryl aldehyde derivative having from 7 to approximately 18 carbon atoms. They can also be fluorinated ketone derivatives, such as hexafluoroacetone, 1,2-dichlorotetrafluoroacetone or 1,1,1-trifluoroacetone, any partially or completely fluorinated ketone derivative with a linear or branched chain having from 3 to approximately 13 carbon atoms and partially or completely fluorinated aryl ketone derivatives having approximately from 8 to 18 carbon atoms in the aryl group or in the group constituting the acetone.

According to a preferred form of the invention, the carbonyl derivative used is trifluoroacetaldehyde, also known as fluoral, in its hydrated or anhydrous form.

It is preferably employed in its hydrated form.

As mentioned above, the compound which it is desired to functionalize according to the invention is an aromatic derivative. In the account which follows of the present invention, the term "aromatic" is understood to mean the conventional notion of aromaticity as defined in the literature, in particular by Jerry March, Advanced Organic Chemistry, 4th edition, John Wiley and Sons, 1992, pp. 40 et seq.

In the context of the present invention, the aromatic derivative can be monocyclic or polycyclic.

In the case of a monocyclic derivative, it can comprise, in its ring, one or more heteroatoms selected from nitrogen, phosphorus, sulfur and oxygen atoms.

According to a preferred embodiment, they are nitrogen atoms.

Mention may in particular be made, by way of illustration of the monocyclic heteroaromatic derivatives capable of being condensed according to the invention, of pyridine derivatives and pyrimidine, pyridazine and pyrazine derivatives.

The claimed process proves to be more particularly effective in condensing heteroaromatic derivatives of pyridine type with the nitrogen atom present at the 3 position with respect to the hydroxyl functional group.

The carbon atoms of the aromatic derivative can optionally be substituted, provided that the carbon or carbons liable to be involved in the condensation reaction remain reactive.

Two vicinal substituents present on the aromatic ring can also form, together with the carbon atoms which carry them, a preferably aromatic hydrocarbonaceous ring comprising, if appropriate, at least one heteroatom. The aromatic derivative is then a polycyclic derivative.

Mention may be in particular be trade, by way of illustration of compounds of this type, of naphthalene and quinoline and isoquinoline derivatives.

Mention may in particular be made, by way of representation of aromatic compounds which are suitable for the present invention, of those corresponding to the general formula I

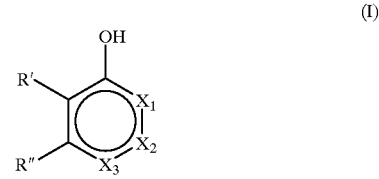

(I)

in which:

$X_1$, $X_2$ and $X_3$ are, independently of one another:
  a heteroatom and preferably a nitrogen atom, or
  —C(R''')=, with R''' being as defined below, and R, R'' and R''' are, independently of one another, a hydrogen atom or an electron-donating substituent or R' and R'' form, together with the carbon atoms which carry them, a preferably aromatic $C_6$ hydrocarbonaceous ring comprising, if appropriate, one or more heteroatoms, with at least one of the R', R'' and R''' groups being a hydrogen atom.

The electron-donating nature of the substituents present on the aromatic derivative is assessed in the context of the present invention according to the scale (for the negative values) defined in the work by Jerry March, "Advanced Organic Chemistry", 3rd edition, chapter 9, pages 243 and 244.

Mention may be made, as examples of preferred electron-donating groups, of $C_1$ to $C_{10}$ alkyls, these being linear or branched, $C_1$ to $C_{10}$ alkoxys, $C_1$ to $C_{10}$ alkyl ethers, amino, mono- or dialkylaminos, or $C_3$ to $C_9$ cycloalkyls or heterocycloalkyls, themselves optionally substituted by a halogen atom or a hydroxyl, amino or mono- or dialkylamino group.

The compound of general formula I preferably comprises a single heteroatom, preferably a nitrogen atom, which is situated at the 3 position with respect to the hydroxyl functional group present on the ring. They can in particular be 3-hydroxypyridine derivatives.

The aromatic compound to be functionalized according to the invention more preferably corresponds to the general formula IA

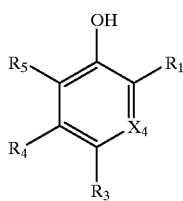

(IA)

in which:
—$X_4$ is a nitrogen atom or —$C(R_2)=$, and
$R_1$, $R_2$, $R_3$, $R_4$ and $R_5$, which are identical or different, are a hydrogen or halogen atom or a group selected from: $C_1$ to $C_{10}$ alkyls, these being linear or branched, $C_1$ to $C_{10}$ alkoxys, $C_1$ to $C_{10}$ alkyl ethers, amino, mono- or dialkylaminos, or $C_3$ to $C_9$ cycloalkyls or heterocycloalkyls, themselves optionally substituted by a halogen atom or a hydroxyl, amino or mono- or dialkylamino group,
or either $R_1$ and $R_2$ or $R_2$ and $R_3$ constitute, with the bond established between them, an aromatic or heteroaromatic ring,
with at least one of the $R_1$, $R_2$, $R_3$, $R_4$ and $R_5$ substituents being a hydrogen atom.

In addition to the required hydroxyl functional group, this aromatic derivative can comprise one or more additional substituents. As mentioned above, they are preferably electron-donating substituents which make it possible to favor the generation of the anionic form of the aromatic derivative in the presence of a base.

Mention may in particular be made, by way of representation of aromatic derivatives which can be efficiently functionalized according to the invention, of cresol, naphthol or 3-hydroxypyridine derivatives, guaiacol, halophenols or phenol derivatives carrying one or more additional hydroxyl functional groups and more preferably derivatives of phenol, 3-hydroxypyridine, naphthol, hydroxyquinoline or hydroxyisoquinoline type.

The condensation of carbonyl compound(s) with the aromatic derivative can be carried out in accordance with the present invention according to two supplemental alternative forms.

According to the first alternative form, this condensation is carried out in the presence of a water-soluble inorganic base. It is more preferably a non-nitrogenous inorganic base.

Inorganic bases, other than nitrogenous bases, have the advantage of being more modest in cost and of being less harmful to the environment. Finally, protection is achieved from any side reaction liable to be observed with primary or secondary amines, for example.

When this base is brought into contact with the aromatic derivative, it must result in the conversion of said compound to its anionic derivative.

To this end, a base differing by at least one $pK_a$ unit and preferably two $pK_a$ units from the anionic form of the aromatic derivative is preferably chosen.

Water-soluble alkali metal salts of hydroxide and carbonate type are more particularly suitable for the invention.

Mention may in particular be made, by way of illustration of these bases, of hydroxides, such as NaOH, KOH or LiOH, and salts of strong bases with a weak acid, such as $K_2CO_3$ and $Na_2CO_3$.

Likewise, the choice of the water-soluble base can be made while taking into account the presence or absence of electron-donating substituents in the aromatic derivative to be functionalized. For example, in the specific case where the compound of general formula I carries one or more electron-withdrawing groups, a weak base may be sufficient to result in its anionic form.

The base used is generally employed in a proportion of at least one equivalent with respect to the aromatic derivative and preferably in a slight excess.

In fact, the amount is to be adjusted according to the degree of condensation desired.

Furthermore, it advantageously proves possible to stereo selectively direct the condensation of the carbonyl compound at the aromatic ring through the choice of the cation, generally a metal cation, associated with the base.

Some cations, such as sodium and lanthanum, favor condensation at the ortho position. Conversely, other cations, such as potassium, direct it more particularly into the para position.

According to this alternative form of the claimed process, the condensation is preferably carried out by gradual introduction of the carbonyl compound into the mixture composed of the aromatic derivative and of the water-soluble base.

In this way, monocondensation is favored.

According to a second alternative form of the invention, the condensation is carried out in the presence of a basic heterogeneous catalyst.

In this specific case, the base used is a heterogeneous catalyst based on hydroxides and/or oxides of metal salts.

It can in particular be magnesia.

It is more preferably a catalyst selected from oxides, hydroxides and basic salts of alkaline earth metals and/or rare earth metals not exhibiting a degree of valency of IV and from the minerals comprising them.

Natural minerals or synthetic analogues which are composed of intercalated layers of metal oxides or hydroxides, such as hydrotalcite, are very particularly suitable for the invention. It more preferably relates to a natural hydrotalcite or a synthetic analogue.

These basic salts comprise various combinations of $M^{2+}$ metal cations, such as $Mg^{2+}$, $Zn^{2+}$, $Cu^{2+}$, $Ni^{2+}$, $Te^{2+}$ or $Co^{2+}$, and trivalent cations of $M^{3+}$ type, such as $Al^{3+}$, $Cr^{3+}$ or $Fe^{3+}$. The anions associated with these metal cations can be halogens, organic anions or oxanions.

Mention may in particular be made, by way of representation of these hydrotalcites, of that corresponding to the formula $[Mg_6Al_2(O_4)_{16}]CO_3 \cdot 4H_2O$.

Likewise, the process for condensation by the basic catalytic route can be carried out using, as catalysts, oxides and carbonates of rare earth metals, such as ytterbium and lanthanum.

The catalyst can generally be introduced in a proportion of 5 to 90%, preferably of 10 to 50%, by weight with respect to the substrate.

According to this second alternative form of the claimed process, the condensation is preferably carried out by introducing the basic heterogeneous catalyst into a mixture of the aromatic derivative and of the carbonyl compound. The condensation is generally carried out while heating the reaction medium at a temperature equal to or greater than 50° C., preferably of between approximately 80 and 120° C. and more preferably of the order of 100 to 110° C.

It also proves possible, according to this alternative form, to favor the condensation toward either the para or ortho position through the choice of the catalyst.

Thus it is that catalysts of the type of hydrotalcites or rare earth metal oxides direct the condensation of the carbonyl compound rather into the ortho position.

On conclusion of the condensation of the carbonyl compound with the aromatic derivative, according to one or other of the two alternative forms of the invention, the expected product or products is/are recovered.

To this end, in the case of a reaction according to the first alternative form, the reaction medium is neutralized at the end of the reaction and the expected compound is extracted according to conventional methods which are thus familiar to a person skilled in the art. When the condensation reaction is carried out in the presence of a basic heterogeneous catalyst, it is sufficient to filter the reaction medium in order to isolate the condensed product.

Generally, it is necessary to purify the condensed product so as to separate it either from the unreacted starting aromatic derivative or from other compounds liable also to be formed during the reaction, such as other mono- or polycondensed aromatic derivatives.

These separation and/or purification operations also come within the competence of a person skilled in the art. They can in particular be chromatographic operations.

The present invention also applies to the compounds obtained according to the claimed process.

It is also directed to a compound of formula (II):

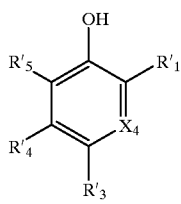

(II)

in which:

$X_4$ is a nitrogen atom or —C($R_2$)═ and

—R'$_1$, R'$_2$, R'$_3$, R'$_4$ and R'$_5$, which are identical or different, are a hydrogen or halogen atom or a group selected from: $C_1$ to $C_{10}$ alkyls, these being linear or branched, $C_1$ to $C_{10}$ alkoxys, $C_1$ to $C_{10}$ alkyl ethers, amino, mono- or dialkylaminos, or $C_3$ to $C_9$ cycloalkyls or heterocycloalkyls, themselves optionally substituted by a halogen atom or a hydroxyl, amino or mono- or dialkylamino group, or either R'$_1$ and R'$_2$ or R'$_2$ and R'$_3$ constitute, with the bond established between them, an aromatic or heteroaromatic ring, with at least two of the R'$_1$, R'$_3$ and R'$_5$ substituents being a group of formula III:

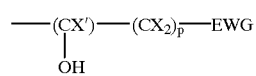

(III)

in which the X units, which are identical or different, are a hydrogen atom, a halogen atom, preferably fluorine, or a radical of formula $C_nX_{2n+1}$ with n being an integer at most equal to 5, preferably to 2;

p is 0 or an integer at most equal to 2;

the X' unit is a hydrogen atom or a group selected from $C_5$ to $C_{18}$ aryls, linear or branched $C_1$ to $C_{13}$ alkyls or linear or branched $C_2$ to $C_{14}$ alkenyls, if appropriate substituted. The substituents can in particular be a hydroxyl group, a halogen atom, a $C_1$–$C_{13}$ alkyl group and/or a amino group; the preferred value for X' is hydrogen;

with the possibility that the X' unit be bonded to one $CX_2$ to form a $C_4$ to $C_8$ ring;

the symbol EWG is an electron-withdrawing group advantageously a fluorine atom or a perfluorinated residue of formula $C_{n'}X_{2n'+1}$ with n' being a integer at most equal to 8, with the proviso that at least one of the X or EWG units present on the carbon α to the hydroxy functional group is a fluorine atom, and with the total number of carbon atoms of the polyfluoroalkyl derivative of formula III between 1 and 15, preferably between 1 and 10.

Preferably —$X_4$ is —C($R_2$)═ with $R_2$ advantageously being hydrogen.

Preferably, the compound of formula II has two groups of formula III and more preferably at the ortho positions. Said two groups of formula III are advantageously the same.

The preferred group of formula III is —CHOH—$CF_3$.

The compound of formula II is preferably 2,6-bis[2,2,2-trifluoro-1-hydroxyethyl]4-methyl-phenol.

More particularly, another subject-matter of the invention is the compounds selected from:

2,2,2-trifluoro-1-(2-hydroxyphenyl)ethanol, 2,2,2-trifluoro-1-(2-hydroxy-5-methylphenyl)ethanol, 2,2,2-trifluoro-1-(2-hydroxy-5-chlorophenyl)ethanol, 2,2-difluoro-1-(2-hydroxyphenyl)ethanol, 2,2-difluoro-1-(4-hydroxyphenyl)ethanol, 2,2,2-trifluoro-4-(3-hydroxypyridinyl)ethanol, and 2,2,2-trifluoro-2-(3-hydroxypyridinyl)ethanol, ethanol, 2,2,2-trifluoro-1-(2-chlorophenyl)ethanol, 2,2-difluoro-1-(2-hydroxyphenyl)ethanol, 2,2-difluoro-1-(4-hydroxyphenyl)ethanol, 2,2,2-trifluoro-4-(3-hydroxypyridinyl)ethanol, and 2,2,2-trifluoro-2-(3-hydroxypyridinyl)ethanol.

The examples which appear below are presented by way of illustration and without implied limitation of the invention.

EXAMPLE 1

2,2,2-Trifluoro-1-(2-hydroxyphenyl)ethanol 15 g (161 mmol) of phenol and 6.4 g of NaOH pellets are introduced into a 100 ml three-necked round-bottomed flask. The mixture is stirred and 22.5 g (145 mmol) of 75% w/w fluoral hydrate in water are added. The mixture is heated to 50° C. and is kept under these conditions for 12 hours. The reaction mixture is cooled. 50 ml of toluene and so ml of water are added. Neutralization is carried out with a 3N HCl solution.

The aqueous phase is separated by settling and then extracted with 2×20 ml of toluene. The organic extracts are dried and quantitatively determined by GC (gas chromatography). The following are thus obtained:

2,2,2-trifluoro-1-(4-hydroxyphenyl)ethanol, RY=42%

2,2,2-trifluoro-1-(2-hydroxyphenyl)ethanol, RY=40%.

EXAMPLE 2

2,2,2-Trifluoro-1-(2-hydroxy-5-5-methyl-phenyl)ethanol 15 g (139 mmol) of p-cresol and 15 ml of 10N sodium hydroxide are introduced into a 100 ml three-necked reactor, the mixture is stirred and 22.5 g (145 mmol) of 75% w/w fluoral hydrate in water are added. The mixture is stirred at 50° C. for 12 hours. After treating the reaction mass as described in Example 1, a yield of 88% of the expected alcohol is obtained for a degree of conversion DC of 95%.

EXAMPLE 3

2,2,2-Trifluoro-1-(2-hydroxynaphthyl)ethanol 10 g (69 mmol) of β-naphthol and 11 g (63.8 mmol) of 75% w/w fluoral hydrate in water were introduced into a 100 ml three-necked reactor. 1.0 g of MgO is added. The mixture is stirred while heating at 105° C. for 5 hours. After treating the reaction mass as described in Example 1, a degree of conversion DC of β-naphthol of 92% is obtained with a yield of 85%.

EXAMPLE 4

2,2,2-Trifluoro-1-(2-hydroxyphenyl)ethanol 9.3 g (100 mmol) of phenol and 3.9 g (25 mmol) of 75% fluoral hydrate are introduced into a 100 ml reactor. 5.0 g of hydrotalcite $Mg_6Al_2(O_4)_{16}.4H_2O$ are added. The mixture is heated at 100° C. for 5 hours. After treating the reaction medium according to the protocol described in Example 1, a yield of 88% of the corresponding alcohol is obtained with an ortho/para ratio equal to 1.

EXAMPLE 5

2,2,2-Trifluoro-1-(2-hydroxy-5-methyl-phenyl)ethanol 11.6 g (100 mmol) of p-cresol and 3.9 g (25 mmol) of 75% fluoral hydrate are introduced into a 100 ml reactor. 5.0 g of MgO are added. The mixture is heated at 100° C. for 6 hours. After treating according to the protocol described in Example 1, a yield of 90% of the expected alcohol is obtained.

EXAMPLE 6

2,6-bis[2,2,2-trifluoro-1-hydroxyethyl]4-methyl-phenol 5.8 g (50 mmol) of p-cresol and 15.5 g (100 mmol) of 75% fluoral hydrate are introduced into a 100 ml reactor. 5 g of MgO are added. The mixture is heated at 105° C. for 8 hours. After treating according to the protocol described in Example 1, 70% of dihydroxyalkylated product are obtained.

EXAMPLE 7

2,2,2-Trifluoro-1-(2-hydroxy-5-chlorophenyl)ethanol 12.5 g (100 mmol) of p-chlorophenol and 3.9 g (25 mmol) of 75% fluoral hydrate are introduced into a 100 ml reactor. 6 g of hydrotalcite $Mg_6AlGa(O_4)_{16}.4H_2O$ are added and the mixture is heated at 100° C. for 7 hours. After treating the reaction medium according to the protocol described in Example 1, a yield of 45% of the expected product is obtained.

EXAMPLE 8

2,2,2-Trifluoro-1-(2-hydroxyphenyl)ethanol 9.3 g (100 mmol) of phenol and 3.9 g (25 mmol) of 75% fluoral hydrate are introduced into a 100 ml reactor. 5.0 g of a catalyst are added and the mixture is heated at 50° C. for 5 hours. The nature of the catalyst employed and the yields of monocondensed products obtained, with their ortho/para ratio, are reported in Table I below.

TABLE I

| Catalyst | RY ortho | RY Para |
| --- | --- | --- |
| $La_2O_3$ | 68% | 8% |
| $Y_2O_3$ | 52% | 14% |
| Hydrotalcite Mg/Al = 3 | 25% | 26% |
| BaO | 18% | 19% |

EXAMPLE 9

2,2-Difluoro-1-(2-hydroxyphenyl)ethanol
2,2-Difluoro-1-(4-hydroxyphenyl)ethanol 9.3 g (100 mmol) of phenol and 4.9 g (25 mmol) of 50% w/w difluoroacetaldehyde hydrate in water are introduced into a 100 ml reactor. 50 g of MgO are added. The mixture is stirred and is heated at 100° C. for 7 hours. The catalyst is filtered off.

A yield of 82% of the two expected alcohols is obtained by analysis by gas chromatography (GC).

EXAMPLE 10

Condensation with 3-hydroxypyridine 9.5 g (100 mmol) of 3-hydroxypyridine and 7.8 g (50 mmol) of 75% fluoral hydrate in water are introduced into a 100 ml reactor. 2.5 g of MgO are added and the mixture is heated at 100° C. while stirring for 8 hours. The catalyst is filtered off at 70° C.

A yield of the expected alcohols of 75% (2 and 4 isomers) is obtained by GC analysis.

What is claimed is:

1. A process for condensing at least one carbonyl compound having at least one electron-withdrawing group with an aromatic compound having at least one hydroxyl functional group, the process comprising condensing the at least one carbonyl compound with the aromatic compound in a basic medium, and wherein the electron-withdrawing group present on the carbonyl compound is a $C_1$–$C_{15}$ fluoroalkyl group, an ester, or a nitrile.

2. The process as claimed in claim 1, wherein the electron-withdrawing group present on the carbonyl compound is a fluoroalkyl group.

3. The process as claimed in claim 1, wherein the electron-withdrawing group present on the carbonyl compound is a fluoroalkyl group of formula:

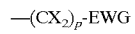

wherein
the two X units are identical or different, and are a hydrogen atom, a halogen atom or a radical of formula $C_nX_{2n+1}$ with n being an integer at most equal to 5;
p is an integer at most equal to 2;
EWG is an electron-withdrawing group, having functional groups that are inert under the reaction conditions, with the proviso that at least one of the X or EWG units present on the carbon α to the carbonyl functional group is a fluorine atom,
and wherein the total number of carbon atoms of the fluoroalkyl group is between 1 and 15.

4. The process as claimed in claim 1, wherein the carbonyl compound additionally carries at the carbonyl functional group a hydrogen atom, a $C_5$ to $C_{18}$ aryl, a linear or branched $C_1$ to $C_{13}$ alkyl, or a linear or branched $C_2$ to $C_{14}$ alkenyl.

5. The process as claimed in claim 1, wherein the carbonyl compound is hydrated or anhydrous trifluoroacetaldehyde.

6. The process as claimed in claim 1, wherein the aromatic compound corresponds to the formula I

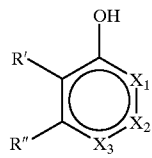

wherein:
$X_1$, $X_2$ and $X_3$ are, independently of one another: C(R'''), and

R, R'' and R''' are, independently of one another, a hydrogen atom or an electron-donating substituent, or R' and R'' form, together with the carbon atoms which carry them, a $C_6$ hydrocarbonaceous ring, and wherein at least one of the R', R'' and R''' groups is a hydrogen atom.

7. The process as claimed in claim 1, wherein the aromatic compound corresponds to the formula IA

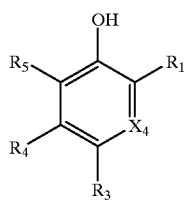

wherein:
$X_4$ is C($R_2$) and
$R_1$, $R_2$, $R_3$, $R_4$ and $R_5$ are identical or different, and are a hydrogen, a halogen atom, a linear or branched $C_1$ to $C_{10}$ alkyl, a $C_1$ to $C_{10}$ alkoxy, a $C_1$ to $C_{10}$ alkyl ether, an amino, a mono- or dialkylamino, or a $C_3$ to $C_9$ cycloalkyl,
or either $R_1$ and $R_2$ or $R_2$ and $R_3$ constitute, with the bond established between them, an aromatic ring, and
wherein at least one of $R_1$, $R_2$, $R_3$, $R_4$ and $R_5$ is a hydrogen atom.

8. The process as claimed in claim 1, wherein the aromatic compound is a phenol or a naphthol.

9. The process as claimed in claim 1, wherein the molar ratio between carbonyl compound and the aromatic compound (carbonyl compound/aromatic compound) is at most ½ equivalent of the aromatic compound.

10. The process as claimed in claim 1, wherein the condensation is carried out in the presence of a stoichiometric deficiency of carbonyl compound.

11. The process as claimed in claim 1, wherein the condensation employs the carbonyl compound in a ratio of 0.25 to 1 equivalents of the aromatic compound.

12. The process as claimed in claim 1, wherein the condensation is carried out in the presence of a stoichiometric excess of carbonyl compound.

13. The process as claimed in claim 1, wherein the condensation employs the carbonyl compound in a ratio of at most 1 to 2 equivalents of the aromatic compound.

14. The process as claimed in claim 1, wherein the condensation is carried out in the presence of a water-soluble inorganic base.

15. The process as claimed in claim 1, wherein the condensation is carried out in the presence of a water-soluble inorganic base which differs by at least one $pK_a$ unit from the anionic form of the aromatic compound.

16. The process as claimed in claim 1, wherein the condensation is carried out in the presence of a water-soluble alkali metal hydroxide salt or alkali metal carbonate salt.

17. The process as claimed in claim 1, wherein the condensation is carried out in the presence of a water-soluble inorganic base in a proportion of at least one equivalent with respect to the aromatic compound.

18. The process as claimed in claim 1, wherein the condensation is carried out in the presence of sodium hydroxide.

19. The process as claimed in claim 1, wherein the condensation is carried out by gradual introduction of the carbonyl compound into a mixture composed of the aromatic compound and a water-soluble base.

20. The process as claimed in claim 1, wherein the condensation is carried out in the presence of a basic heterogeneous catalyst.

21. The process as claimed in claim 1, wherein the condensation is carried out in the presence of a basic heterogeneous catalyst, wherein the basic heterogeneous catalyst comprises a metal salt hydroxide, a metal oxide salt, or a mixture thereof.

22. The process as claimed in claim 1, wherein the condensation is carried out in the presence of a basic heterogeneous catalyst, wherein the basic heterogeneous catalyst comprises hydroxides and/or other basic salts of alkaline earth metals and/or rare earth metals or of the minerals comprising them, with the proviso that the rare earth metals do not exhibit a valency of IV.

23. The process as claimed in claim 1, wherein the condensation is carried out in the presence of a magnesia as heterogeneous catalyst.

24. The process as claimed in claim 1, wherein the condensation is carried out in the presence of a basic heterogeneous catalyst, wherein the basic heterogeneous catalyst is a natural hydrotalcite or a synthetic analogue thereof.

25. The process as claimed in claim 1, wherein the condensation is carried out in the presence of a basic heterogeneous catalyst, wherein the basic heterogeneous catalyst is ytterbium oxide, ytterbium carbonate, lanthanum oxide, or lanthanum carbonate.

26. The process as claimed in claim 1, wherein the condensation is carried out in the presence of a basic heterogeneous catalyst, wherein the basic heterogeneous catalyst is present in a proportion of 10% to 50% by weight with respect to the aromatic compound.

27. The process as claimed in claim 1, wherein the condensation is carried out by introducing a basic heterogeneous catalyst into a mixture of the aromatic compound and of the carbonyl compound.

28. The process as claimed in claim 1, wherein the condensation is carried out by introducing a basic heterogeneous catalyst into a mixture of the aromatic compound and of the carbonyl compound and by heating the reaction medium at a temperature of greater than or equal to 50° C.

29. The process as claimed in claim 1, wherein the product or products resulting from the condensation of at least one carbonyl compound with the aromatic compound are recovered by extracting after neutralizing the reaction medium or filtering without neutralizing, and wherein a basic heterogeneous catalyst is employed.

30. The compound obtained by employing the process as claimed in claim 1.

31. A compound of formula II:

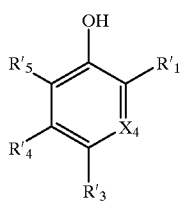

wherein:
$X_4$ is $C(R'_2)$ and
$R'_1$, $R'_2$, $R'_3$, $R'_4$, and $R'_5$, which are identical or different, are a hydrogen, a halogen atom, a linear or branched $C_1$ to $C_{10}$ alkyl, a $C_1$ to $C_{10}$ alkoxy, a $C_1$ to $C_{10}$ alkyl ether, an amino, a mono- or dialkylamino, or a $C_3$ to $C_9$ cycloalkyl,
or either $R'_1$ and $R'_2$ or $R'_2$ and $R'_3$ constitute, with the bond established between them, an aromatic ring, and
wherein at least two of the $R'_1$, $R'_3$ and $R'_5$ substituents are each a group of formula III:

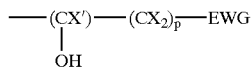

wherein
the X units are identical or different and are a hydrogen atom, a halogen atom, or a radical of formula $C_nX_{2n+1}$ with n being an integer at most equal to 5; and
p is an integer at most equal to 2; and
the X' unit is a hydrogen atom, a $C_5$ to $C_{18}$ aryl, a linear or branched $C_1$ to $C_{13}$ alkyl, or a linear or branched $C_2$ to $C_{14}$ alkenyl; and
EWG is an electron-withdrawing group;
with the proviso that at least one X unit or EWG present on the carbon a to the hydroxy functional group is a fluorine atom, and wherein the total number of carbon atoms of the fluoroalkyl group of formula III is between 1 and 15.

32. A compound according to claim 31, wherein X' is hydrogen.

33. A compound according to claim 31, wherein $R_2$ is hydrogen.

34. A compound according to claim 31, wherein the compound contains two groups of formula III.

35. A compound according to claim 31, wherein the compound contains two groups of formula III in ortho position.

36. A compound according to claim 31, wherein the group of formula III is —CHOH—$CF_3$.

37. The compound which is
2,6-bis(2,2,2-trifluoro-1-hydroxyethyl)4-methyl-phenol,
2,2,2-trifluoro-1-(2-hydroxyphenyl)ethanol,
2,2,2-trifluoro-1-(2-hydroxy-5-methylphenyl)-ethanol,
2,2,2-trifluoro-1-(2-hydroxy-5-chlorophenyl)ethanol,
2,2-difluoro-1-(2-hydroxyphenyl)ethanol, or
2,2-difluoro-1-(4-hydroxyphenyl)ethanol.

38. The process of claim 3, wherein EWG is a fluorine atom or a perfluorinated residue of formula $C_{n'}X_{2n'+1}$ wherein n is an integer of at most 8.

39. The process of claim 38, wherein n is 5.

40. The process of claim 6, wherein R' and R" form an aromatic $C_6$ hydrocarbonaceous ring.

41. The process of claim 7, wherein the linear or branched $C_1$ to $C_{10}$ alkyl, the $C_1$ to $C_{10}$ alkoxy, the $C_1$ to $C_{10}$ alkyl ether, the amino, the mono- or dialkylamino, or the $C_3$ to $C_9$ cycloalkyl is substituted by a halogen atom, a hydroxyl group, an amino group, or a mono- or dialkylamino group.

42. The process of claim 9, wherein the molar ratio is at most ¼ equivalents of the aromatic compound.

43. The process of claim 11, wherein the ratio of carbonyl compound to aromatic compound is 0.25 to 0.5 equivalents.

44. The process of claim 13, wherein the ratio of carbonyl compound to aromatic compound is at most 1 to 1.25 equivalents.

45. The compound of claim 31, wherein the linear or branched $C_1$ to $C_{10}$ alkyl, the $C_1$ to $C_{10}$ alkoxy, the $C_1$ to $C_{10}$ alkyl ether, the amino, the mono- or dialkylamino, or the $C_3$ to $C_9$ cycloalkyl is substituted by a halogen atom, a hydroxyl group, an amino group, or a mono- or dialkylamino group.

46. The compound of claim 31, wherein at least one X unit is a fluorine atom.

47. The compound of claim 31, wherein at least one X unit is a radical of formula $C_nX_{2n+1}$, wherein n is 2.

48. The compound of claim 31, wherein X' is a $C_5$ to $C_{18}$ aryl, a linear or branched $C_1$ to $C_{13}$ alkyl, or a linear or branched $C_2$ to $C_{14}$ alkenyl, wherein the aryl, alkyl or alkenyl is substituted by a hydroxyl group, a halogen atom, a $C_1$-$C_{11}$ alkyl group and/or an amino group.

49. The compound of claim 31, wherein the X' unit is bonded to one $CX_2$ to form a $C_4$ to $C_8$ ring.

50. The compound of claim 31, herein EWG is a fluorine atom or a perfluorinated residue of formula $C_{n'}X_{2n'+1}$, wherein n' is an integer of at most 8.

51. The compound of claim 31, wherein the total number of carbon atoms of the fluoroalkyl group of formula III is between 1 and 10.

* * * * *

UNITED STATES PATENT AND TRADEMARK OFFICE
CERTIFICATE OF CORRECTION

PATENT NO. : 6,541,674 B2
DATED : April 1, 2003
INVENTOR(S) : Roland Jacquot and Michel Spagnol It is certified that error appears in the above-identified patent and that said Letters Patent is hereby corrected as shown below:

<u>Title page,</u>
Items [21] and [22], please insert the following items:

-- [21] Appl. No. 98/06848,
 [22] Filed May 29, 1998, --

Signed and Sealed this

Fourteenth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,541,674 B2
DATED : April 1, 2003
INVENTOR(S) : Roland Jacquot and Michel Spagnol It is certified that error appears in the above-identified patent and that said Letters Patent is hereby corrected as shown below:

<u>Title page,</u>
Please insert the following item:

-- [30]  Foreign Application Priority Data
    May 29, 1998 (FR) . . . . . . . . . . . . 98/06848 --

This certificate supersedes Certificate of Correction issued October 14, 2003

Signed and Sealed this

Thirtieth Day of December, 2003

JAMES E. ROGAN
*Director of the United States Patent and Trademark Office*